(12) United States Patent
Berggren et al.

(10) Patent No.: US 7,208,532 B2
(45) Date of Patent: Apr. 24, 2007

(54) MANUFACTURE OF IMPROVED SUPPORT MATRICES

(75) Inventors: Eva Berggren, Uppsala (SE); Dag Lindstrom, Vattholma (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 517 days.

(21) Appl. No.: 10/168,709

(22) PCT Filed: Dec. 11, 2000

(86) PCT No.: PCT/EP00/12479

§ 371 (c)(1),
(2), (4) Date: Sep. 9, 2002

(87) PCT Pub. No.: WO01/48420

PCT Pub. Date: Jul. 5, 2001

(65) Prior Publication Data

US 2003/0144127 A1    Jul. 31, 2003

(30) Foreign Application Priority Data

Dec. 28, 1999    (SE) .................................. 9904801

(51) Int. Cl.
| | | |
|---|---|---|
| C08F 2/46 | (2006.01) | |
| C08F 251/00 | (2006.01) | |
| C08J 3/28 | (2006.01) | |
| B01J 20/04 | (2006.01) | |
| B01J 20/24 | (2006.01) | |

(52) U.S. Cl. .................... 522/89; 522/150; 522/152; 522/153; 522/158; 522/160; 522/157; 522/88; 522/113; 522/120; 522/121; 522/178; 522/182; 527/300; 527/306; 527/309; 527/313; 502/400; 502/401; 502/404; 502/439; 502/527.18

(58) Field of Classification Search .................... 522/1, 522/6, 86, 85, 84, 87, 88, 89, 113, 120, 121, 522/150, 178, 182, 153, 157, 152, 158; 527/200, 527/201, 207, 300, 306, 309, 313; 502/400, 502/401, 404, 439, 527.18

See application file for complete search history.

(56) References Cited

U.S. PATENT DOCUMENTS

| | | | |
|---|---|---|---|
| 3,715,342 A | | 2/1973 | Colomb |
| 4,046,720 A | | 9/1977 | Rembaum et al. |
| 4,094,833 A | | 6/1978 | Johansson |
| 4,170,685 A | * | 10/1979 | Rembaum et al. .......... 428/402 |
| 4,224,359 A | | 9/1980 | Rembaum et al. |
| 4,981,625 A | * | 1/1991 | Rhim et al. .................. 264/13 |

FOREIGN PATENT DOCUMENTS

| | | |
|---|---|---|
| WO | WO 96/03147 A | 2/1996 |
| WO | WO 00/03800 A | 1/2000 |

OTHER PUBLICATIONS

Database WPI, Section Ch, Week 198419, Derwent Publications Ltd., London, GB AN 1984-119044 XP002165609 and SU 1 033 181 A (Zibarev P V) Aug. 7, 1983.

Database WPI, Section Ch, Week 199407, Derwent Publications Ltd., London, GB AN 1994-051149 XP002165623 and JP 05 337368 A (Fuso Chem Ind Co Ltd) Dec. 21, 1993.

* cited by examiner

Primary Examiner—Sanza L. McClendon
(74) Attorney, Agent, or Firm—Yonggang Ji

(57) ABSTRACT

A method for the production of a cross-linked support matrix that in form of a bed will permit liquid flow velocities above 5 cm/h, preferably above 50 cm/h, to pass through the bed. The method is characterized in that it comprises the steps: (a) providing a starting support matrix that has pendent unsaturated groups, and (b) subjecting said starting support matrix to electron beam or gamma-ray irradiation. The use of a cross-linked support matrix produced by a method comprising the steps of: (a) providing a starting support matrix that has pendent unsaturated groups, and (b) subjecting said starting support matrix to electron beam or gamma-ray irradiation as a support matrix in liquid chromatography, cell culturing, step-wise solid phase synthesis of organic compounds, running catalytic reactions by the use of a solid phase bound catalyst.

15 Claims, No Drawings

MANUFACTURE OF IMPROVED SUPPORT MATRICES

TECHNICAL FIELD

The present invention concerns a new method for the manufacture of porous support matrices to be used
(a) as separation media,
(b) in cell culturing,
(c) in step-wise solid phase synthesis of organic compounds,
(d) in catalytic reactions by the use of a solid phase bound catalyst (e.g. enzymes and their cofactors, coenzymes etc).

The use as separation media includes size separations, such as liquid filtration, size exclusion chromatography etc, and adsorption based separations. Separation processes include chromatographic processes and batch-wise processes. Cell culturing means culture of cells on microcarriers. The uses given above in particular refer to uses in which the support matrix is in form of a bed through which a liquid flow can pass (compare the third objective below). The beds may be monolithic or in form of particles that are packed or fluidised. Fluidised beds include fully mixed beds (stirred dispersions, suspensions etc) to stabilized fluidised beds.

BACKGROUND TECHNOLOGY

Support matrices of the type given above are typically in form of porous monolithic beds or porous or non-porous particles. The support particles may be used in fluidised beds or packed beds. In order to reach a sufficient rigidity, the matrices often have to be cross-linked.

Typical problems associated with support matrices for the above-mentioned uses are:
(a) high flow velocities may lead to an increased back pressure which ultimately causes collapse of the matrix;
(b) when in particle form, the matrices may have a tendency not to withstand mechanical forces during packing in columns and other reaction vessels;
(c) tricky to manufacture; and
(d) the matrices may need a separate sterilization.

One previous way of manufacturing support matrices that have an improved rigidity is to start from a polymer carrying nucleophilic groups and groups that have a masked electrophilic reactivity activating the masked groups and permitting the electrophilic and nucleophilic groups to react with each other. The polymer is typically a polysaccharide. See WO 9738018 (Amersham Pharmacia Biotech AB).

Another recent method is to heat a polymeric support matrix carrying residual unsaturated groups. This method is in particular adapted to support matrices obtained by polymerisation of mixtures comprising vinyl aryl monomers, aryl or methacryl monomers or other unsaturated monomers. See International Patent Application PCT/SE99/0126 (Amersham Pharmacia Biotech AB).

WO 9726071 (Amersham Pharmacia Biotech AB) and WO 9700255 (Amersham Pharmacia Biotech AB) include electron beam irradiation and gamma-ray irradiation as two out of many examples for initiating polymerisation of unsaturated groups in order to manufacture support matrices for various uses.

EP 534016 (W.R. Grace & Co) describes chromatographic matrices with thermoresponsive properties. The publication suggests that one could cross-link beads consisting of linear polymers by irradiation with light, electron rays and gamma rays. It is also suggested that linear polymer after adsorption to a base matrix could be crosslinked in the same way.

WO 9603147 (Fidia Advanced Biopolymers) suggests production of gels and biocompatible substrates by electron beam irradiation of a polymer funtionalized with a plurality of unsaturations. The uses are as carriers in drug administration, as biocompatible substrates for cell culture in three-dimensional systems etc.

EP 159694 (E.I. Du Pont de Nemours) suggests electron beam irradiation for the production of gels from monomers with one and two polymerisable unsaturations.

There are no demands on withstanding liquid flow on the monolithic or packed bed formats of the matrices described in WO 9603147 and EP 159694.

OBJECTIVES OF THE INVENTION

A first objective is to provide improved methods for manufacturing support matrices as defined above, which methods are more efficient and simpler than previous methods.

A second objective is to provide methods that give support matrices of the kind discussed above that will
(a) permit high flow rates with a low risk for collapse when in bed form, and
(b) have a high mechanical resistance and rigidity (hardness), i.e. to reduce the problems discussed under the heading "Background technology", and
(c) give a sterile product.

A third objective is to provide a new manufacturing method for porous support matrices that have a swellability and hardness (rigidity) permitting liquid flow velocities above 5 cm/h, such as above 50 cm/h and typically below 3000 cm/h to pass through a bed built up of the porous support matrix during at least one hour (chromatographic conditions, packed bed where appropriate). The liquid referred to is selected among those commonly in use for liquid chromatography, for instance aqueous. The pores are typically as defined below. For monolithic matrices there is always present a pore system enabling convective mass transport through the matrix (convective pore system). For support matrices in particle form either or both of pore systems discussed below may be present (convective pore system and diffusive pore system).

THE INVENTION

It has now been discovered that these objectives can be accomplished by a method, which is characterized by comprising the steps of:
(a) providing a starting support matrix that has pendant unsaturated groups, and
(b) subjecting the starting support matrix to electron beam (EB) or gamma-ray irradiation.

By the term "unsaturated group" is contemplated a group that is able to polymerise and form an extended carbon chain comprising four or more carbon atoms that pair wise derive from the unsaturated group. A typical example is a carbon-carbon double bound, for instance a vinyl group ($CH_2=CH-$) that may have one or more of its hydrogen substituted.

Irradiation (Step (b))

The use of high-energy radiation, such as electron beam radiation and gamma radiation is a powerful method to initiate polymerisation of "unsaturated groups". A difference between gamma radiation and electron beam radiation is the ability to penetrate material. Gamma photons from $^{60}Co$ interact weakly and have the ability to deeply penetrate material before they loose their energy. Electrons from an accelerator penetrate the material to a depth, which is dependent on the particle energy and the density of the material. The penetration depth can approximately be estimated with the following formula: E/3* (cm), where E is the electron energy in MeV and is the density of the material to be irradiated. The radiation intensity is much higher for electron beam radiation than for gamma radiation. Therefor the irradiation times are shorter for electron beam radiation.

When using radiation to initiate polymerisation or cross-linking it is important to set the limits for radiation dose (Mrad). Usual doses are between 0.1–20 Mrad depending on the application. The required dose is dependent on the type of polymer to be treated and the monomer to be polymerised by the irradiation. Also the presence of ions, such as $Cu^{2+}$, $Fe^{3+}$ etc, and liquids are important parameters to take into consideration when setting the radiation dose. It is also important to control the atmosphere surrounding the substrate to be irradiated. Presence of oxygen may lead to oxidation and degradation of the polymer. The practitioner will know how to set up and optimise the process in order to control the resulting product.

The main previous use of high-energy radiation is for sterilisation of different products, e.g. medical disposable.

Step (b) may be carried out in the presence of compounds carrying one or more unsaturated groups. Typical these compounds are selected amongst polyhydroxy polymers substituted with groups comprising unsaturation as discussed below and low molecular weight compounds having one or two unsaturated groups. Polymers of this kind are likely to introduce so-called extenders or tentacles into the matrix.

Step (a): The Starting Support Matrix

The starting support matrix may be manufactured by per se known methods, for instance by (1) polymerising a mixture of monomers carrying one or more unsaturated groups; or
(2) transforming a base polymer to a starting support matrix which carries a plurality of groups in which there are unsaturation. There are two main routes for introduction of the unsaturation onto the base polymer:
   (2a) prior, and
   (2b) subsequent to the transformation of the base polymer to the starting support matrix.

In alternative (1) at least one of the monomers carries two or more unsaturated groups (monomer $I^1$). Typical examples are divinyl aryls, such as divinyl benzenes, and bisforms of acrylates and acrylamides. There may also be present monomers that carry only one unsaturated group (monomer $II^1$).

In alternative (2a) the base polymer carrying a plurality of unsaturated groups is called monomer $I^{2a}$. Monomers that carry only one unsaturated groups may also be present (monomer $II^{2a}$).

In alternative (2b) one starts from suitable base polymer and convert it by per se known methods to a form that can be used as support matrix in any of the above-mentioned fields. If needed the base polymer is allowed to cross-link. The unsaturated groups are then inserted on the support matrix formed from the base polymer.

Suitable base polymers in alternatives 2a and 2b are hydrophilic in the sense that they are soluble or insoluble but swellable in water (below 30° C.). The hydrophilic property of the polymer is based on the presence of polar groups such as hydroxy, amino, carboxy, esters, amido etc. Examples of hydrophilic polymers are polysaccharides, such as agarose, dextran, cellulose, starch, pullulan, etc and synthetic polymers, that are based on polymerisation reactions that formally can be looked upon as condensation reactions between monomers comprising two or more groups selected from nucleophilic groups and electrophilic groups. Typical nucleophilic groups in this context are hydroxy, amino etc. Typical electrophilic groups are epoxides, epihalohydrines, vicinal dihalides, acyl halides etc.

Monomer $I^1$ and monomer $I^{2a}$ (alternative 1 and 2a, respectively) comprise two or more unsaturated groups and are non-polymeric with a low molecular weight (monomer $I^1$) or are polymers (monomer $I^{2a}$). The amounts of monomer $I^1$ and monomer $I^{2a}$ are typically are in the interval of 1–100%, such as 20–100% or 1–50% of the total amount of polymerisible monomers. The amounts depend on the intended use of the final support matrix, other monomers, etc. The percentage is in weight-% (w/w).

Monomer $II^1$ and monomer $II^{2a}$ (alternative (1) and (2a), respectively) are often low molecular weight compounds, by which is contemplated a non-polymer having a molecular weight less than 5,000 dalton, such as less than 2,000 dalton. Specific examples of compounds that can be used as monomer $II^1$ or monomer $II^{2a}$ are vinyl benzenes, monoacrylic and monomethacrylic acid, ester, amide and nitrile.

Each of monomer $I^1$, monomer $I^{2a}$, monomer $II^1$ and monomer $II^{2a}$ may be a mixture of different monomers that have one unsaturated group (monomer $II^1$ and monomer $II^{2a}$) or two or more unsaturated groups (monomer $I^1$, monomer $I^{2a}$).

The polymerisation in alternatives (1) and (2a) may be carried out as well known in the field. Various forms of starting support matrices may be achieved. See for instance U.S. Pat. No. 4,094,833.

Unsaturated groups are easily introduced into the base polymer used in alternatives (2a) and (2b) by reacting them with bifunctional reagents carrying both an unsaturated group and a reactive electrophilic group, for instance an epoxide. See for instance WO 9726071 and WO 9700255. Particularly interesting groups comprises an allyl structure or a styryl structure (including styryl ether structure).

Manufacture of the starting support matrix according to alternative 1 may include that polymerisation is initiated by electron beam irradiation or gamma irradiation. In such a variant of the invention, step (a) and step (b) may be carried out consecutively without interruption or as two separate consecutive steps. Between step (a) and step (b) there may be a change in irradiation dosing. Between the two steps extra monomers as discussed above may be added, working up steps may be inserted etc.

The starting support matrix (alternatives 1, 2a and 2b) may easily be obtained in a predetermined form, e.g. monolithic or in form of particles and/or with pore sizes as known in the field. The mean particle size of the starting support matrices used in the present method may thus be in the interval from 1–1000 μm such as 1–300 μm or 10–300 μm. The particles may be polydispersed (polysized) or monodispersed (monosized). By a monodispersed (monosized) population of particles is meant that more than 95% of the particles have sizes within 0.95M–1.05M where M is the mean diameter of the particles of the population. Particle populations that are not monodispersed are polydispersed. Particles may have regular or more or less irregular shape. Examples of different shapes are fibres and more or less spherical particles (beads).

The pores of the support matrices may be of different sizes. In principle there are two kinds of pore systems: (a) a pore system permitting convective mass transport (convective pore system), and (b) a pore system permitting only diffusive transport (diffusive pore system).

System (a) has pore sizes $\geq 0.1$ µm, such as $\geq 0.5$ µm, by which is meant that a sphere $\geq 0.1$ µm respective $\geq 0.5$ µm in diameter is able to pass through. An applied liquid flow will be able to flow through this pore system. In case the support matrix is in form of beads packed to a bed, the ratio between the pore sizes of the convective pore system and the diameter of the particles typically is in the interval 0.01–0.3, with preference for 0.05–0.2. Pores having sizes $\geq 0.1$ µm, such as $\geq 0.5$ µm, are often called macropores.

Pore system (b) is typically only available to a through flowing liquid by diffusive mass transport. Typically the openings of this pore system into the convective pore system are such that only spheres with diameters $\leq 0.5$ µm, such as $\leq 0.1$ µm, can pass through. Pores having sizes $\leq 0.5$ µm, such as $\leq 0.1$ µm, are often called micropores.

The figures for pore sizes given in the context of the present invention refer to values obtained by SEM or ESEM (scanning electron microscopy and environmental scanninmg electron microscopy, respectively) and/or by SEC (size exclusion chromatography) utilising polystyrenes and dextrans, for instance. See Hagel, "Pore Size Distribution" in "Aqueous Size-Exclusion Chromatography" Elsevier Science Publisher B.V., Amsterdam, The Netherlands (1988) 119–155.

The ranges discussed above for particle sizes and pore sizes of the starting support matrix are also applicable to the support matrices obtained by the present inventive method. By properly matching the properties of the starting support matrices with the input of energy in the electron beam or gamma-ray irradiation, it will in principle be possible to produce support matrices having predetermined particle size and pore size distributions by the instant inventive method.

THE INTRODUCTION OF FUNCTIONAL GROUPS

Functional groups may be introduced into the support matrix obtained according to the invention. One kind of functional groups is based on affinity binding (affinity adsorption) and is best represented by a member of an affinity pair. Well-known affinity pairs are
  (a) positively and negatively entities (ion exchange; the immobilised entity being selected among primary, secondary, tertiary and quaternary ammonium, sulphonate, sulphate, phosphonate, phosphate, carboxy etc groups),
  (b) antibodies and antigens/haptens,
  (c) lectins and carbohydrate structures,
  (d) IgG binding proteins and IgG,
  (e) pair of hydrophobic groups,
  (f) polymeric chelators and chelates,
  (g) complementary nucleic acids,
  (h) cells and cell binding ligands, etc.

Affinity members also include entities participating in catalytic reactions, for instance enzymes, enzyme substrates, cofactors, co-substrates etc. Members of cell-cell and cell-surface interactions and a synthetic mimetics of bio-produced affinity members are also included.

In case the functional group to be introduced on the support matrix is insensitive to electron beam and/or gamma-ray irradiation, the group can be present already on the starting support matrix.

In case the final matrix has extenders the functional groups may be attached to the extenders and/or to the base matrix.

The invention is further defined in the appending patent claims and will now be further illustrated by a number of non-limiting patent examples.

EXPERIMENTAL

1. The Synthesis of Polymers Carrying Unsaturated Groups.
   Dextran: Allyl dextran Mw 150,000 was synthesized by reacting allylglycidyl ether with dextran mw 150,000 to a substitution degree of 1.2–1.5 mmol allyl groups/g dry substance. The method was in principle the same as described in WO 9726071 and WO 9700255. Allyldextran Mw 2,000,000 and were synthesized by the analogous method
   Agarose: See parts 5.a and 5.c.

2. Electron Beam (EB) Irradiation of Samples.
   The irradiation was performed on an Electron Beam Microtron 7.5 MeV (Inst. of Acceleratorteknik, Royal Technical High School, Stockholm, Sweden). The samples to be irradiated were placed on a conveyor belt, which is transported under the radiation source. The dose settings were estimated through calorimetric measurements made by the operator.

3. Support Matrices Based on Allyl Dextran. Gel Formation in Petri Dishes.

3a.1 Gels from allyldextran and N,N'-methylenebisacrylamide by free radical polymerisation and post-curing with electron beam irradiation (EB). 15.0 g of allyldextran (150,000, allyl conc. 1.2–1.5 mmol/g dry substance) was dissolved in 75 ml of distilled water through stirring in room temperature for 2–4 hours, until a clear solution was obtained. 25 ml of methanol and 3.0 g of N,N'-methylenebisacrylamide were added and stirred a couple of minutes. 15.0 g of the solution was added to a Petri dish (5 cm) and nitrogen gas was added through a capillary. Finally 0.1 g APS was mixed with the solution and 0.07 ml TEMED was added. Polymerization was allowed to proceed at 50° C. for 2 hours. The obtained gel was named "15% allyldextran and 3% N,N'-methylenebisacryl amide" and used as a reference gel. The calculation is based on the weight of allyldextran and bisacrylamide, respectively, to the volume of water and methanol. The gel was also post-cured with EB. The hardness (of the reference gel was measured with Stevens LFRA Texture analyser (Metric Stevens, England).

The same procedure was followed for gels with the composition of 15% allyldextran+1% ($\Leftrightarrow$ 1 g) N,N'-methylenebisacrylamide, and 15% allyldextran+0% N,N'-methylenebisacrylamide. These gels were post-cured with EB.

3.a.2. Gels of Allyldextran and N,N'-methylenebisacrylamide by Direct Polymerisation by EB.
   This example was the same as for (a) above except that APS and TEMED were omitted. Gels of allyldextran of Mw 2,000,000 were also produced by direct initiation with electron beam irradiation. The procedure was the same as described above.

None of the samples (3.a.1 and 3.a.2) were purged with nitrogen before irradiation. The top of the gel is therefor in contact with air and some oxidation could occur.

3.b. Measurement of Hardness (Rigidity)—Gels in Petri-dishes (3.a.1 and 3.a.2). The hardness of the obtained gels was measured with Stevens LFRA Texture analyser (Metric Stevens, England). The samples were still kept in the Petri-dishes and the load (g) for penetrating the gel 1 mm with a speed of 0.5 mm/s was registered.

For series 3.a.1 the change in hardness after EB irradiation of gels which had been pre-polymerised with APS and TEMED in Petri-dishes is presented in table 1. For the mixture of "15% allyldextran+3% N,N'-methylenebisacryl amide" the increase in hardness is three-fold and for the sample without N,N'-methylenebisacrylamide the increase is 20 times. It is assumed that the effect is due to higher degree of cross-linking.

TABLE 1

Measurements of hardness of gels in Petri-dishes.

| Sample 15% Allyldextran (Mw 150 000) + % bisacrylamide | Radiation dose (Mrad) | Hardness, load (g) for 1 mm |
|---|---|---|
| 0% | 0 | 16 |
| 0% | 3 | 330 |
| 1% | 0 | 76 |
| 1% | 3 | 390 |
| 3% | 0 | 140 |
| 3% | 3 | 430 |

In series 3.a.2 a comparison is made for gels, which are directly polymerized with EB. The dosage for these gels was 3 Mrad. The molecular weight of dextran was 150,000 and 2,000,000) and the amount of bisacrylamide varied (0, 1 and 3%). The gels made of dextran 2,000,000 are in general harder, and as shown before the concentration of bisacrylamide has a great impact of the mechanical properties, table 2.

TABLE 2

Measurements of hardness of gels in Petri-dishes.

| Sample 15% Allyl dextran + % bisacrylamide | Allyl Dextran Mw 150 000 | Allyl Dextran Mw 2000000 | Radiation dose (Mrad) | Hardness Load (g) for 1 mm |
|---|---|---|---|---|
| 0% | X |   | 3 | 120 |
| 0% |   | X | 3 | 180 |
| 1% | X |   | 3 | 250 |
| 1% |   | X | 3 | 340 |
| 3% | X |   | 3 | 530 |
| 3% |   | X | 3 | 610 |

4. Preparation and Evaluation of Particles Based on Allyldextran and N,N'-Methylenebisacrylamide.

4.a Particles from Allyldextran and N,N'-Methylenebis Acrylamide. Free Radical Polymerisation Followed by Postcuring by EB.

75 g of fine grade chalk coated with stearate, 5.0 g anionic surfactant and 1,000 ml heptane were charged in a round bottomed flask. The mixture was heated to 50° C. 100.0 g allyl dextran (150,000 as produced above), 10.0 g N,N'-methylenebisacrylamide and 5.0 g APS were dissolved in the same manner as mentioned above in 500 ml water and 150 ml methanol. The solution and heptane were brought together and stirred for 10 minutes at 50° C. in a nitrogen gas atmosphere. 4.5 ml TEMED was added and the reaction was continued for 4 hours at 50° C. Insoluble gel beads having a size of 25–200 μm were obtained. The product was washed with acetic acid, ethanol and distilled water. The sample is named "15% allyldextran and 1.5% bisacrylamide". See part 3.a.1 for meaning of percentage. Other particles were produced and named in a similar way.

The particles were sampled in plastic bottles, sealed and purged with nitrogen. The bottles were placed flat under the radiation source. The height of the slurry to be irradiated was about 1–2 cm. In table 3 the different samples and radiation doses are presented.

TABLE 3

Samples and radiation doses.

| Sample | Sample no. | Dose (Mrad) |
|---|---|---|
| 10.5% allyldextran (Mw 150 000) + 15% bisacrylamide | 1 | 0 |
| 10.5% allyldextran (Mw 150 000) + 15% bisacrylamide | 2 | 2 |
| 10.5% allyldextran (Mw 150 000) + 15% bisacrylamide | 3 | 4 |
| 15% allyldextran (Mw 150 000) + 1.5% bisacrylamide | 4 | 0 |
| 15% allyldextran (Mw 150 000) + 1.5% bisacrylamide | 5 | 2 |
| 15% allyldextran (Mw 150 000) + 1.5% bisacrylamide | 6 | 4 |
| 15% allyldextran (Mw 2 000 000) + 0% bisacrylamide | 7 | 0 |
| 15% allyldextran (Mw 2 000 000) + 0% bisacrylamide | 8 | 2 |
| 15% allyldextran (Mw 2 000 000) + 0% bisacrylamide | 9 | 4 |

4.b. Titration of Allyl Groups Estimation of Dry Weight of 1 ml Media.

1 ml of the various samples were taken out and transferred to a 100 ml suction flask and water was added to a total volume of 10 ml. Thereafter bromine was added during stirring until the colour remained. After bromination the flask is set under vacuum until the sample is colourless. The sample is transferred to a titration vessel and water is added to a total volume of 30 ml. 1–2 drops of $HNO_3$ (conc.) is added and the titration is performed with 0.1 M $AgNO_3$. The result is achieved as mmol allyl groups/ml sample.

After titration the same samples were washed with water and ethanol on a glass filter. The samples were dried in oven at 110° C. over night or for the agarose particles at 70° C. for 18 h, and the dry weight of 1 ml media was determined. The concentration of allyl groups per gram dry weight was then calculated, table 4.

For all three samples there is an obvious decrease in allyl group content after EB treatment.

TABLE 4

Allyl concentration and dry weight for different particles at different dosages of EB.

| Sample No Dose | Allyl conc. μmol/ml | Dry weight* (g/ml) | Allyl/gram dry weight, μmol/g |
|---|---|---|---|
| 1; ref** | 111 | 0.170 | 660 |
| 2; 2 Mrad | 53 | 0.150 | 350 |
| 3; 4 Mrad | 44 | 0.156 | 280 |
| 4; ref** | 88 | 0.0970 | 900 |
| 5; 2 Mrad | 96 | 0.190 | 510 |
| 6; 4 Mrad | 87 | 0.204 | 430 |
| 7; ref** | 49 | 0.0320*** | 1680 |
| 8; 2 Mrad | 56 | 0.107 | 520 |
| 9; 4 Mrad | 44 | 0.139 | 320 |

*The dry weight was measured on samples that had been titrated for determining allyl groups.
**reference
***The dry weight was measured on samples that had not been titrated.

4.c. Particle Size Distribution.

The distribution was determined with the Shimadzu SALD-1000 (laser diffraction) which measures the volume percentage for different intervals and the results is expressed as $d_{50}$ (cumulative particle diameter for 50% of the sample).

A comparison of the particle diameters was made before and after the electron beam irradiation, se table 5. For exp. no. 1–3 the particle size did not change at all. Though for exp. no. 4–6 and 7–9 the particle size was decreased and especially for exp. no. 7–9 which do not contain any bisacrylamide.

TABLE 5

Particle size distribution for different particles at different radiation doses.

| Sample No | Allyl-Dextran % | $M_w$ | Bisacrylamide % | Dose Mrad | $Dp_{50}$ [μm] |
|---|---|---|---|---|---|
| 1 | 10.5 | $1.5 \times 10^5$ | 15 | 0 | 61 |
| 2 | 10.5 | $1.5 \times 10^5$ | 15 | 2 | 60 |
| 3 | 10.5 | $1.5 \times 10^5$ | 15 | 4 | 61 |
| 4 | 15 | $1.5 \times 10^5$ | 1.5 | 0 | 78 |
| 5 | 15 | $1.5 \times 10^5$ | 1.5 | 2 | 66 |
| 6 | 15 | $1.5 \times 10^5$ | 1.5 | 4 | 62 |
| 7 | 15 | $2 \times 10^6$ | 0 | 0 | 109 |
| 8 | 15 | $2 \times 10^6$ | 0 | 2 | 54 |
| 9 | 15 | $2 \times 10^6$ | 0 | 4 | 51 |

4.e. Gel Filtration

Gel filtration properties were determined for one prototype before and after irradiation. The media was packed in a HR 10/15 column (Amersham Pharmacia Biotech AB, Uppsala, Sweden) and the porosity was determined with the following proteins: Cytochrome C, β-Lactoglobulin, HSA, IgG, Ferritin, Thyroglobulin. Kav values were calculated for the proteins. See Hagel, "Pore Size Distribution" in "Aqueous Size-Exclusion Chromatography" Elsevier Science Publisher B.V., Amsterdam, The Netherlands (1988)119–155.

Method:
Flow rate: 0.20 ml/min (15 cm/h)
Buffer: 0.1 M Tris, 0.5 M NaCl, pH 8.0
Sample concentration:

| | |
|---|---|
| Thyroglobulin | 2 mg/ml |
| Ferritin | 2 mg/ml |
| IgG | 2 mg/ml |
| HSA | 4 mg/ml |
| Cytochrome C | 0.8 mg/ml |
| β-Lactoglobulin | 4 mg/ml |

Void: Blue Dextran 0.2%
Sample volume: 200 μl

The EB treated gel had become more porous in this case, table 6.

TABLE 6

$K_{AV}$ for the gel from sample no. 1 and 3 (before respective after EB irradiation).

| Proteins | $K_{AV}$; Sample no 1 (0 Mrad) | $K_{AV}$; Sample no. 3 (4 Mrad) |
|---|---|---|
| Cytochrome C | 0.48 | 0.59 |
| β-Lactoglobulin | 0.22 | 0.50 |
| HSA | 0.10 | 0.39 |
| IgG | | 0.26 |
| Ferritin | | 0.16 |
| Thyroglobulin | | 0.04 |

4.f. Flow Properties

The gels were packed in an XK 16 column and the testing was performed by flow rate stepwise. The pressure drop was recorded for each flow rate and the maximum flow rate before collapse was noted. The result is presented in Table 7. Within the radiation doses tested the collapsing flow-rate has increased between 100–400%.

TABLE 7

Pressure-flow rate properties for particles of allyldextran and bisacrylamide irradiated at different doses.

| Sample no. | Allyl dextran, $M_w = 1.5 \times 10^5$ (%) | Bis acrylamide (%) | Dose Mrad | Collapse Flow rate cm/h |
|---|---|---|---|---|
| 1 | 10.5 | 15 | 0 | 750 |
| 2 | 10.5 | 15 | 2 | 1500 |
| 3 | 10.5 | 15 | 4 | 1650 |
| 4 | 15 | 1.5 | 0 | 15 |
| 5 | 15 | 1.5 | 2 | 60 |
| 6 | 15 | 1.5 | 4 | 90 |

5. Preparation of Gel Samples Based on Allyl Agarose

5.a. Allylation of Agarose Particles

EXAMPLE A 180 g of 50% NaOH, 1.2 g of $NaBH_4$ and 39 g $Na_2SO_4$ were added under stirring to a reactor containing 300 ml base matrix (Sepharose 6FF, Amersham Pharmacia Biotech, Uppsala, Sweden). The mixture was heated to 50° C. 150 ml of allylglycidyl ether was added. The reaction was permitted to continue for 16 h at 50° C. The mixture were then neutralised with acetic acid (pH=6–7) and the matrix washed with distilled water, ethanol and distilled water again.

Analysis showed 0.17 mmol allyl groups/ml of gel. The particles were subjected to bromination and cross-linking (4.b) or EB treatment (f).

EXAMPLE B

Analogous to Example A. 180 g of 50% NaOH, 1.2 g of $NaBH_4$, 39 g $Na_2SO_4$, 300 ml base matrix and 300 ml of allyl glycidyl ether.

Analysis showed 0.29 mmol allyl groups/ml of gel. The particles were subjected to EB treatment (5.f).

5.b. Bromination of Allylated Agarose Particles and Cross-linking

Bromination: 23 g $NaAc \times 3H_2O$ (sodium acetate) was added to a reactor containing a solution of 140 ml allylated gel (drained gel from (a) Example A) and 40 ml distilled water under stirring. After 5 min bromine-water ($Br_2/H_2O$)

was added to the solution until a dark yellow colour were obtained and maintained for over 1 min. The reaction continues for approximately 15 min. Thereafter sodium formiate was added, giving the gel white colour.

Cross-linking: 5 g $Na_2SO_4$ was added to a reactor containing the brominated gel. After 1 h 14 g 50% NaOH and 0.02 g $NaBH_4$ were added to the slurry. The reaction temperature were increased to 40° C. and the reaction was allowed to continue for 16 h. The gel was washed with distilled water until the pH=7.

The particles were evaluated regarding pressure-flow properties (5. h) and gel filtration properties (5.i).

5.c. Preparation of Allylated Particles.

An agarose solution were prepared in a batch reactor by adding 60 g agarose to 900 ml distilled water under stirring for 2 h at 95° C. The solution was cooled to 70° C. 4.5 ml NaOH 50%, 0.14 g $NaBH_4$ and 12 ml allylglycidyl ether were added. The reaction continues for 2 h under stirring at 70° C. The solution were then neutralised with 60% acetic acid and HCl (pH=7–8).

The emulsion media was made in an emulsion reactor by adding 60 g ethyl cellulose (N-50 emulsifier) to 1.050 ml toluene under stirring at 60° C. (the dissolving of N-50 emulsifier in toluene takes approximately 2 h).

The agarose was transferred to the emulsion media. The stirring was regulated to 100 rpm. Agarose gel particles were thereby formed and variation of the rotation speed of the stirrer and the addition of extra N-50 emulsifier can control their sizes.

The desired maximal particle size of agarose beds was 120 µm. If the agarose gel particles are too large the rotation speed can be increased up to 220 rpm and extra N-50 emulsifier can be added. Taking samples, which are analysed in a microscope with a built-in size graduation, checks the maximal particle size. Once the 120 µm is reached, the slurry is cooled down. The slurry were cooled from 60° C. to <25° C. in approximately 30 min. The gel was washed with ethanol 99.5% and distilled water.

The particles were further cross-linked with epichlorohydrin (5.d) following by EB treatment (5.f) or bromination and cross-linking (5.e).

Or the EB treatment (5.f) was made prior to the cross-linking with epichlorohydrin (5.g).

5.d. Cross-linking of allylated gel with epichlorohydrin. 340 g $Na_2SO_4$ were added to a reactor containing a mixture of 700 ml gel (drained gel from 5.c) and 300 ml distilled water under stirring. The reaction temperature was increased to 50° C. and after 1 h, 15 g 50% NaOH and 1 g $NaBH_4$ were added to the slurry as well as 105 g 50% NaOH and 75 ml epichlorohydrin, which were added during a period of 6–8 h. The reaction was allowed to continue over night. The gel was washed with distilled water and 60% acetic acid to obtain a pH =5–7.

The particles were further cross-linked according to 5.e or cross-linked with EB treatment (5.f).

5.e. Bromination of Allylated Agarose Particles and Cross-linking

Bromination: Analogous to (b). 25 g $NaAcx3H_2O$ (sodium acetate), 110 ml epichlorohydrin cross-linked gel (drained gel from 5.d).

Cross-linking: Analogous to (5.b). 5 g $Na_2SO_4$, 15 g 50% NaOH and 0.02 g $NaBH_4$ The particles were analysed regarding pressure-flow properties (5.h) and gel filtration properties (5.i).

5.f. Electron Beam Irradiation of Allyl Agarose Particles.

See above under 4.a. In table 8 the samples and doses are listed. The samples are named according to the method used of preparation.

TABLE 8

Samples and radiation doses.

| Sample name | Sample No. | Dose(Mrad) |
|---|---|---|
| a-reference (not allylated) | 1 | 0 |
| a-reference (not allylated) | 2 | 3 |
| a-Example A | 3 | 3 |
| a-Example B | 4 | 3 |
| C | 5 | 3 |
| c + d | 6 | 3 |

5.g. Cross-linking with Epichlorohydrin of EB Treated Allyl Agarose Particles.

Particles from 5.c that had been EB treated according to 5.f were further cross-linked with epichlorohydrin. Analogous to 5.d: 340 g of $Na_2SO_4$, 100 ml drained gel (from 5.f, sample 5), 43 ml distilled water, 2 g 50% NaOH, 0.15 g $NaBH_4$, 15 g 50% NaOH and 11 ml epichlorohydrin.

5.h. Pressure-Flow Properties

The gels were packed in a HR 10/30 column and the testing was performed by increasing the flow rate stepwise. The pressure drop was recorded for each flow rate and the maximum flow rate before collapse was noted. See table 9.

The results show that the EB treatment of allylated agarose particles has a great impact of the pressure-flow properties. Compared to bromination the EB treatment is equal or better.

TABLE 9

Pressure-flow rate properties of agarose gels.

| Sample name; Preparation and cross-linking methods | Collapsed Flow rate (cm/h) |
|---|---|
| a-reference | 1220 |
| a-reference + f | 1140 |
| a-example A + f | 3040 |
| a-example A + b | 2280 |
| a-example B + f | 3800 |
| c + d | 2280 |
| c + d + f | >3800 |
| c + f + g | 3420 |
| c + d + e | 3420 |

5.i. Gel filtration properties of agarose particles. Gel filtration properties were determined for the agarose prototypes before and after irradiation. The media was packed in a HR 10/30 column (Amersham Pharmacia Biotech AB, Uppsala, Sweden) and the porosity was determined with the following proteins: BSA, Ferritin, Thyroglobulin, IgG, R-nasA. $K_{av}$ values (See Hagel, "Pore Size Distribution" in "Aqueous Size-Exclusion Chromatography" Elsevier Science Publisher B.V., Amsterdam, The Netherlands (1988) 119–155) were calculated for the proteins, see table 10.

Method:

Flow rate: 0.20 ml/min (15 cm/h)

Buffer: 50 mM Na-phosphate, 150 mM NaCl, pH 7.0

Void: Blue Dextran 0.2%

Sample volume: 50 µl

Sample concentration: 10 mg/ml

TABLE 10

Gel filtration of agarose particles.

| Sample name; Preparation and cross-linking method | Kav Thyro | Kav Ferritin | Kav IgG | Kav BSA | Kav RNAse |
|---|---|---|---|---|---|
| a-reference | 0.39 | 0.51 | | 0.69 | 0.88 |
| a-reference + f | 0.36 | 0.46 | | 0.61 | 0.77 |
| a-Example A + f | 0.44 | 0.61 | | 0.71 | 0.93 |
| a-Example A + b | 0.42 | | 0.59 | | 0.77 |
| a-Example B + f | 0.44 | 0.72 | | 0.71 | 0.93 |
| c + d | 0.39 | 0.58 | | 0.71 | 0.90 |
| c + d + f | 0.36 | 0.51 | | 0.62 | 0.85 |
| c + d + e | 0.36 | | 0.57 | | 0.74 |
| c + f + g | 0.45 | 0.60 | | 0.73 | 0.90 |

CONCLUSIONS

It has been shown that beads of allyl dextran and bisacrylamide can be post-cured by electron beam irradiation which led to beads with increased pressure-flow rate properties. The more mechanically stable particles are probably due to a higher degree of cross-linking than what is achieved by polymerisation with APS and TEMED alone. It has been shown that the amount of allyl groups is decreased during the EB treatment. For particles made with a small amount of bisacrylamide, or particles of 100% allyldextran, the particle size was decreased significantly during the EB-treatment. This was not the case for particles of the composition 10.5% allyldextran and 15% bisacrylamide. The particles made from 100% allyl dextran became more opaque upon the EB-treatment probably due to the large degree of skrinkage. The gel filtration properties were evaluated for one gel before and after irradiation. The EB treated gel consist of larger pores than the reference.

For particles of allylated agarose EB treatment was compared to other cross-linking methods such reaction with epichlorohydrin and Br/OH— respectively. Also combinations of the methods were evaluated. It has been shown that electron beam radiation is a powerful method to initiate cross-linking of allylated agarose. The improvement regarding pressure flow rate properties are better or equal compared to the other methods. Gel filtration of the treated particles showed none or a minor change in porosity.

What is claimed is:

1. A method for the production of a cross-linked support matrix in form of a porous monolith or particles that packed to a chromatographic bed will permit liquid flow velocities above 5 cm/h, preferably above 50 cm/h, to pass through the bed for at least 1 hour, comprising the steps of:
   (a) providing a starting support matrix that has pendent unsaturated groups, and
   (b) subjecting said starting support matrix to electron beam or gamma-ray irradiation to effect crosslinking, wherein the staring support matrix has been obtained by polymerizing a mixture of monomers carrying one or more unsaturated groups, at least one of said monomers carrying two or more unsaturated groups (monomer I).

2. The method of claim 1, wherein the starting support matrix has been produced by other means than by polymerisation caused by electron beam irradiation or gamma-irradiation.

3. The method of claim 1, wherein said starting support matrix is subjected to electron beam irradiation and that the dose is selected within the interval 0.1–20 Mrad.

4. The method of claim 1, wherein at least one of said monomers in the mixture carries one unsaturated group (monomer II).

5. The method of claim 1, wherein monomer I comprises a polyhydroxy polymer substituted with a plurality of unsaturated groups and/or a non-polymer low molecular weight monomer carrying two or three unsaturated groups.

6. The method of claim 1, wherein monomer I comprises a polyhydroxy polymer substituted with a plurality of unsaturated groups.

7. The method of claim 4, wherein
   (a) monomer I comprises monomers selected from the group consisting of (i) divinyl aryls, (ii) compounds having two vinyl aryls groups, (iii) compounds having two acryl groups or two methacryl groups, (iv) compounds having two allyl groups, (v) compounds having two vinyl ether groups, and (vi) compounds having two N-vinyl carboxamide groups, and
   (b) monomer II comprises monomers selected from the group consisting of (i) compounds having one vinyl aryl, (ii) compounds having one acryl or methacryl group, (iii) compounds having one allyl group, (iv) compounds having one vinyl ether group, and (v) compounds having one N-vinyl carboxamide groups.

8. A cross-linked support matrix for use as a support matrix in liquid chromatography, cell culturing, step-wise solid phase synthesis of organic compounds, running catalytic reactions by the use of a solid phase bound catalyst in form of porous monolith or particles produced by a method comprising the steps of:
   (a) providing a starting support matrix that has pendent unsaturated groups, and
   (b) subjecting said starting support matrix to electron beam or gamma-ray irradiation, wherein the staring support matrix has been obtained by polymerizing a mixture of monomers carrying one or more unsaturated groups, at least one of said monomers carrying two or more unsaturated groups (monomer I).

9. The matrix of claim 8, wherein said starting support matrix is subjected to electron beam irradiation and that the dose is selected within the interval 0.1–20 Mrad.

10. The matrix of claim 8, wherein at least one of said monomers in the mixture carries one unsaturated group (monomer II).

11. The matrix of claim 8, wherein monomer I comprises a polyhydroxy polymer substituted with a plurality of unsaturated groups and/or a non-polymer low molecular weight monomer carrying two or three unsaturated groups.

12. The matrix of claim 8, wherein monomer I comprises a polyhydroxy polymer substituted with a plurality of unsaturated groups.

13. The matrix of claim 10, wherein
   (a) monomer I comprises monomers selected from the group consisting of (i) divinyl aryls, (ii) compounds having two vinyl aryls groups, (iii) compounds having two acryl groups or two methacryl groups, (iv) compounds having two allyl groups, (v) compounds having two vinyl ether groups, and (vi) compounds having two N-vinyl carboxamide groups, and
   (b) monomer II comprises monomers selected from the group consisting of (i) compounds having one vinyl aryl group, (ii) compounds having one acryl or methacryl group, (iii) compounds having one allyl group, (iv) compounds having one vinyl ether group, and (v) compounds having one N-vinyl carboxamide groups.

14. The method of claim 6, wherein said polyhydroxy polymer is a polysaccharide.

15. The matrix of claim 12, wherein said polyhydroxy polymer is a polysaccharide.

* * * * *